United States Patent [19]

Osipow et al.

[11] Patent Number: 5,308,643
[45] Date of Patent: May 3, 1994

[54] SELF-LATHER GENERATING SHAVING COMPOSITIONS

[76] Inventors: Lloyd I. Osipow, 9875 Harbour Lake Cir., Boynton Beach, Fla. 33437; Dorothea C. Marra, 107 Fernwood Rd., Summit, N.J. 07901; J. George Spitzer, 184 Bradley Pl., Palm Beach, Fla. 33480

[21] Appl. No.: 983,179
[22] Filed: Nov. 30, 1992
[51] Int. Cl.$^5$ .............................................. A61K 7/15
[52] U.S. Cl. ........................................ 424/73; 424/70; 514/945
[58] Field of Search ...................... 424/73, 70; 514/945

[56] References Cited

U.S. PATENT DOCUMENTS 4,744,979  5/1988  Osipow et al. ........................ 424/73
5,186,857  2/1993  Ramirez et al. ...................... 252/167

Primary Examiner—Thurman K. Page
Assistant Examiner—James M. Spear
Attorney, Agent, or Firm—Morgan & Finnegan

[57] ABSTRACT

A shaving preparation is provided that boils above about 50° C. and that rapidly generates a stable shaving lather when rubbed on the skin. The composition is an aqueous soap (a neutralized fatty acid) solution containing a foam generating ingredient, a non-volatile, water-insoluble organic liquid and free fatty acids. Thus, the fatty acids mixture of this invention consists of both free fatty acids and neutralized fatty acids (soap). An unexpected rise in the boiling point occurs when the total fatty acids present are in an amount greater than 11% by weight and where 50 to 85% by weight of the total fatty acids are neutralized fatty acids.

5 Claims, 2 Drawing Sheets

SELF-LATHER GENERATING SHAVING COMPOSITIONS

BACKGROUND OF THE INVENTION

Compositions that produce lather for shaving have been known for many decades. One type of known shaving composition that has been used for years is whisked with a brush to incorporate air and thereby generate lather.

Another type of known lather producing shaving composition is aerosol shaving compositions containing volatile organic liquids under super atmospheric pressure. Such compositions are disclosed in U.S. Pat. No. 2,655,489 to Spitzer et al. In these lather producing compositions, the vapor pressure of the volatile liquids is substantial, say 25 to 40 P.S.I.G. so that the compositions are immediately converted to lather when released from the aerosol container to the atmosphere.

A more recent type of lather producing shaving composition is the gel lather producing composition disclosed in U.S. Pat. No. 3,541,581 to Monson. In the compositions of this patent there are employed organic liquids with vapor pressures of 6 to 14 P.S.I.G. According to the Monson patent, the compositions when released from their container would quickly expand to a lather if not for the inclusion of a gelling agent which restrains lather formation until the shaving composition is applied to the skin in the form of a gel.

More particularly, the Monson compositions are post foaming shaving gel compositions that are dispensed as gels, but produce a lather when rubbed on the face. The compositions comprised a soap solution, a gelling agent, and an organic liquid having a vapor pressure from about 6 to 14 P.S.I.G. at a temperature from about 90 to 100F. The organic liquid is the post foaming agent.

In order to dispense Monson's compositions with their super-atmospheric vapor pressures in the form of gels, it is necessary to employ an especially complex and expensive aerosol container, that in addition to the usual components also includes a bag or piston or equivalent device, as shown in FIG. 4 of the Monson patent.

While Monson states that his post-foaming gels can be packaged in collapsible metal tubes, this is not practical. Because of the super-atmospheric pressure of the compositions, it is necessary to use an aerosol valve and dispensing spout. If a tube cap were used, the composition would continue to gush from the container until the cap was screwed into place. Further, the crimped end of the collapsible tube would unravel and pop open under sustained pressure of the composition. In addition, the pressure would maintain the collapsible metal tube in a constantly expanded state, regardless of the amount of material in the tube. As a consequence, as the contents were emptied, the gel would tend to expand to fill the tube, and then be expelled as an aerated gel or lather.

The Monson compositions because of their above atmospheric vapor pressure cannot be exposed to elevated temperature in storage, shipping and use without causing problems of premature expansion.

This invention relates to shaving compositions which are improvements over those of our U.S. Pat. No. 4,744,979. The latter patent provided shaving compositions with sub-atmospheric vapor pressures that generate a lather when rubbed on the face, and that can be packaged in inexpensive containers, such as collapsible tubes, without premature expansion of the tube during storage, shipment and use.

In the examples of that patent, n-pentane was employed as the lather-generating agent. Superfatting agents and small amounts of somewhat higher boiling hydrocarbons, such as hexane, were employed to raise the boiling point or the organic phase. N-pentane boils at 36° C., and with these additives the boiling point could be raised to about 40° C. The use of larger amounts of these vapor pressure depressants adversely affected lather formation and lather stability.

There is need to raise the boiling point of the compositions to at least about 50° C. Temperatures approaching this can be encountered during shipping and storage. In addition, substantial pressure can develop in the container as the boiling point is approached. Such pressures can cause the seals on conventional collapsible tubes to burst, if such pressures are maintained for an extended period of time.

TABLE 1

| Composition | Fatty Acids plus Surfactants, % | Fatty Acids, % | Free Fatty Acids, % | Mineral Oil % | Boiling Point °C. | Increase Over Expected Boiling Point °C. |
|---|---|---|---|---|---|---|
| A | 11.5 | 7.7 | 4.2 | 3.0 | 41 | 1 |
| B | 12.8 | 12.8 | 4.9 | 2.9 | 45 | 3 |
| C | 13.1 | 9.3 | 4.2 | 2.9 | 45 | 4 |
| D | 13.5 | 9.7 | 1.7 | 2.9 | 46 | 5 |
| E | 14.6 | 10.8 | 3.8 | 2.9 | 48 | 7 |
| F | 15.6 | 11.8 | 4.2 | 2.9 | 46 | 5 |
| G | 16.1 | 12.3 | 2.5 | 5.5 | 50 | 10 |
| H | 16.2 | 14.6 | 4.6 | 7.6 | 55 | 10 |
| I | 15.4 | 15.4 | 5.0 | 4.5 | 56 | 11 |
| J | 16.3 | 14.6 | 4.5 | 5.3 | 57 | 12 |
| K | 16.4 | 14.7 | 4.4 | 6.6 | 56 | 12 |
| L | 15.8 | 15.8 | 5.0 | 4.5 | 57 | 12 |
| M | 16.8 | 14.9 | 5.1 | 4.5 | 59 | 15 |

All percentages are by weight based on the total weight of composition
All compositions contain approximately 4.5% isopentane
Soap is triethanolamine palmitate-cocoate
Surfactant is lauroyl diethanolamide
Mineral oil has a viscosity of 4 cs at 38 C.

TABLE 2

| Composition | Fatty Acids Plus Surfactants, % | Fatty Acids, % | Free Fatty Acids, % | Oil % | Boiling Point °C. | Increase over Expected Boiling Point °C. |
|---|---|---|---|---|---|---|
| N | 14.8 | 11.0 | 4.0 | (1) 6.7 | 49 | 5 |
| O | 14.8 | 11.0 | 4.0 | (2) 6.7 | 47 | 6 |
| P | 14.8 | 11.0 | 4.0 | (3) 6.7 | 49 | 7 |
| Q | 14.8 | 11.0 | 4.0 | (4) 6.7 | 49 | 9 |
| R | 14.8 | 11.0 | 4.0 | (5) 6.7 | 45 | 6 |
| S | 14.6 | 12.8 | 6.1 | (1) 6.7 | 56 | 9 |
| T | 14.6 | 12.9 | 6.1 | (2) 6.7 | 53 | 9 |
| U | 14.6 | 12.7 | 6.1 | (3) 6.7 | 54 | 10 |
| V | 15.4 | 15.4 | 5.0 | (1) 4.5 | 50 | 8 |
| W | 15.4 | 15.4 | 5.0 | (2) 4.5 | 48 | 9 |
| X | 15.4 | 15.4 | 5.0 | (3) 4.5 | 49 | 8 |
| I | 15.4 | 15.4 | 5.0 | (6) 4.5 | 56 | 11 |

All percentages are by weight based on the total weight of composition
All compositions contain approximately 4.5% isopentane
N,O,P,Q,R,V,W,X,Y - Soap is triethanolamine palmitate-cocoate
S,T,V - Soap is diethanolamine palmitate-cocoate
N,O,P,Q,R,S,T,U - Surfactant is lauroyl diethanolamide
(1) isopropyl myristate
(2) Corn oil
(3) dimethyl polysiloxane, 10 cs at 25 C.
(4) isocetyl alcohol
(5) lauryl lactate
(6) mineral oil, 4 cs at 38 C.

TABLE 3

| Composition | Fatty Acids plus Surfactants, % | Fatty Acids, % | Free Fatty Acids, % | Oil (Type) % | Boiling Point, °C. | Increase over Expected Boiling Point °C. |
|---|---|---|---|---|---|---|
| Y | 14.8 | 11.0 | 4.0 | (—). 0 | 39 | 3 |
| Z | 15.7 | 11.9 | 4.2 | (1). 0.9 | 40 | 2 |
| AA | 15.6 | 11.8 | 4.2 | (1). 1.9 | 46 | 7 |
| BB | 15.6 | 11.8 | 4.2 | (1). 2.9 | 48 | 7 |
| CC | 15.6 | 11.8 | 4.2 | (2). 3.0 | 47 | 6 |
| DD | 15.6 | 11.8 | 4.2 | (3). 3.0 | 46 | 5 |
| EE | 15.6 | 11.8 | 4.2 | (1). 1.1 | 50 | 5 |

All percentages are by weight based on the total weight of composition
EE contains approximately 4.5% n-pentane. all other compositions contain approximately 4.5% isopentane
All compositions: surfactant is lauroyl diethanolamide and soap is triethanolamine palmitate-cocoate
(1) mineral oil. 4 cs at 38 C.
(2) mineral oil. 7 cs at 38 C.
(3) mineral oil. 21 cs at 38 C.

It is an object of the instant invention to provide a shaving preparation that, when rubbed on the beard develops a shaving cream lather within a few seconds, i.e., within about ten seconds. Another object is that the shaving cream lather should be both voluminous and stable. An additional object is that the composition that is used to form the shaving cream lather should not boil below about 50° C.

GENERAL DESCRIPTION OF THE INVENTION

The objects of this invention can be realized by combining an aqueous soap solution containing a high concentration of partially neutralized fatty acids with a nonvolatile, water-insoluble organic liquid and a normally liquid foam-generating agent. With this combination of ingredients, there is an unexpectedly large increase in the boiling point of the composition. Surprisingly, the ease with which the lather is formed as well as the lather volume and lather stability are not adversely affected to any material extent by this increase in the boiling point.

Were it not for this discovery, it would have been necessary to use large amounts of water-insoluble organic liquids to act as vapor pressure depressants for the foam-generating agent and thereby raise the boiling point. This would have an important negative effect on the ease of lather formation and on the volume and stability of the lather as well as on the stability of the composition.

It has long been known that aqueous soap (neutralized fatty acid) solutions do not influence the vapor pressure, and therefore the boiling point, of water-insoluble, volatile organic liquids emulsified in the aqueous solution. The accepted explanation is that the aqueous soap solution and the organic liquid are in separate phases. A component must be in the same phase as the organic liquid in order to influence its vapor pressure.

Now it has been unexpectedly found that aqueous soap (neutralized fatty acid) solutions can produce an elevation in the boiling point above that contributed by those organic compounds that can be expected to be in the same phase as the volatile organic liquid that functions as the foam-generating agent. The organic compounds that can be expected to be in the same phase as the foam generating agent include free fatty acids as well as any other oil-soluble organic compounds, such as mineral oil, that may be present in the composition.

In the case of triethanolamine soaps, this excess increase in the boiling point starts to appear when the composition contains about 11% of fatty acids (neutralized fatty acids and free fatty acids) based on the total weight of the composition. The excess boiling point elevation then increases about 2° C. more or less for each 1% increase in total fatty acids, reaching about 13° C. with 16% total of fatty acids in the composition.

BRIEF DESCRIPTION OF THE DRAWINGS

The invention can be more clearly understood by reference to the Figures and tables.

In Table 1 boiling points are reported for each of the compositions shown. The last column of the table shows the increase in the boiling point over the value expected from the presence of free fatty acids and mineral oil dissolved in the organic phase. The latter value was obtained by first calculating the percent of foam-generating agent present in the organic phase of the composition assuming that all of the foam-generating agent, the nonvolatile, water-insoluble organic liquid and the free fatty acids were in that phase. The expected boiling point was then obtained from the appropriate curve of FIG. 1. The increase in boiling point over the expected value is the contribution of the aqueous soap solution to the boiling point elevation. This increase in boiling point as shown in Table 1 is plotted in FIG. 2.

Figure 2:
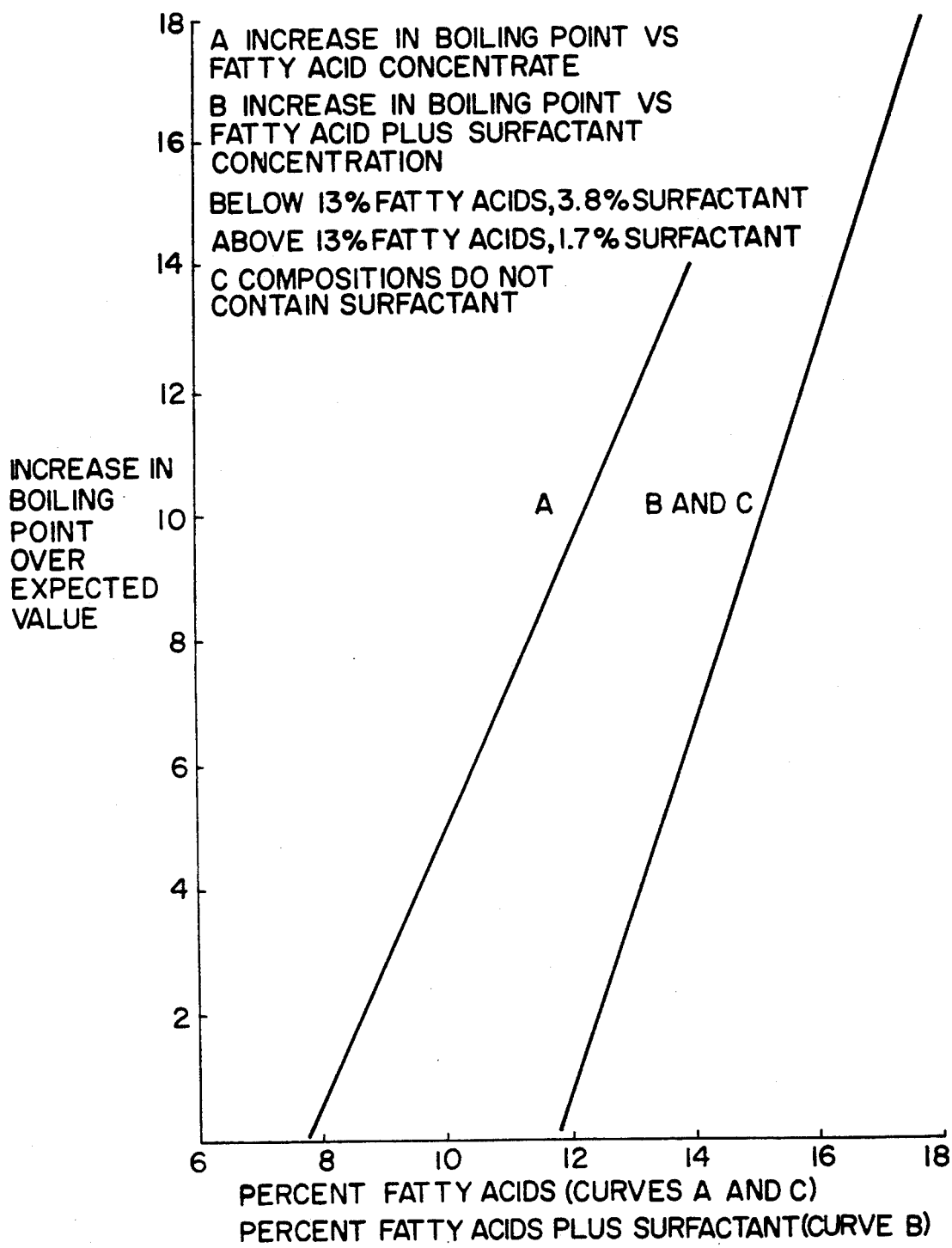

Referring to FIG. 2, curve C is a plot of compositions containing free fatty acids and soap (neutralized fatty acids) without any synthetic surfactant present. It is necessary to have more than 11% by weight of total fatty acids (free and neutralized) based on the weight of the composition before there is an increase in the boiling point above the expected value.

Curves A and B in FIG. 2 refer to the same compositions, which contain lauroyl diethanolamide in addition to free fatty acids and soap (neutralized fatty acids). The difference is that for Curve A, the abscissa is the percent total fatty acids in the compositions, while for Curve B, the abscissa is the percent total fatty acids plus surfactant in the composition. Comparison of these curves with Curve C shows that where a portion of the total fatty acids is replaced by surfactant the surfactant also contributes to the increase in the boiling point over the expected value. However, the increase in boiling point contributed by the surfactant is not necessarily the same as for the fatty acids it replaced.

All of the data were obtained using a grade of isopentane with a boiling point of 30° C. and a grade of n-pentane with a boiling point of 36° C.

The essential components of the invention, i.e., the aqueous soap solution, the foam-generating agent, and the nonvolatile water-insoluble organic liquid will now be discussed in further detail.

A. Aqueous Soap Solution

The aqueous soap solution is of such nature and in such amount that when combined with a suitable nonvolatile water-insoluble organic liquid, it promotes the volatilization of the foam generating agent to form a stable lather when rubbed on the beard in a practical period of time, i.e., within about 10 seconds; in addition, the soap solution contributes to the boiling point elevation of the foam generating agent so that the boiling point of the composition is about 50° C.

To meet these requirements, the aqueous soap solution should contain from about 14 to about 20% by weight of fatty acids (neutralized fatty acids and free fatty acids), based on the total weight of the composition.

From about 50-85% of the fatty acids should be neutralized to form water-soluble soaps, with the remainder present as free fatty acids.

With 14% fatty acids in the composition and employing a range of 50-85% of neutralized fatty acids of the total fatty acid mixture (neutralized fatty acids and free fatty acids), the boiling point will be about 6 degrees C. greater than the expected value. Beyond the range of 50-85% of the fatty acids neutralized to form soap, and 15 to 50% of the fatty acids as free fatty acids, lathering speed, lather volume and lather stability all tend to deteriorate.

The water soluble soaps should consist predominantly of palmitate and/or stearate soaps. However, as the concentration of total fatty acids in the composition is increased, it is advantageous to use increasing amounts of laurate and/or myristate soaps. Otherwise the soap solutions could become too heavy-bodied, and this could present difficulties in manufacture. Examples of suitable water-soluble soaps are stearate, palmitate, myristate and laurate soaps of potassium, ammonium, mono-, di-, and tri-ethanolamine, mono-, di-, and tri-isopropanolamine, 2-amino-2-methyl-1-propanol, and mixtures of these water-soluble soaps.

The preferred soaps are the triethanolamine soaps of predominantly palmitic and/or stearic acid, with 20 to 40% of the fatty acids unneutralized and present as free fatty acids.

The free fatty acids have several functions. They act as vapor-pressure depressants. They enhance lather volume and lather stability and they contribute to the body of the lather, so that the lather has a heavy body, rather than feeling light and air. Other ingredients called superfatting agents have a similar effect. These are water-insoluble compound with a long hydrocarbon chain and a polar group at or near one end of the chain, and include cetyl alcohol, myristyl alcohol, glyceryl monopalmitate, glyceryl monostearate, propylene glycol monopalmitate and propylene glycol monostearate.

Synthetic surface-active agents or surfactants may be used in place of a part of the fatty acids in the compositions. Surfactants also contribute to the increase in the boiling point above the anticipated value. They may also be included to achieve other beneficial effects. These include promoting the volatilization of the foam-generating agent so that the lather is produced more quickly, reducing the tendency of the foam-generating agent to cause smarting, and promoting the formation of a gel. The composition should preferably contain more fatty acids than surfactants.

It has been found that the larger the sum of neutralized acids and free fatty acids plus surfactants if present the greater the increase in the boiling point over the expected value.

The portion of fatty acids that can be replaced by surfactant will depend on the fatty acids present and their concentrations, as well as the choice of surfactant. In general, up to about 35% of the fatty acids may be replaced by surfactant.

Examples of preferred surfactants are nitrogen containing surface active agents selected from the group consisting of:

(a) Tertiary amine oxides with one long hydrocarbon chain of 12 to 22 carbon atoms. Examples of suitable materials include lauryl dimethyl amine oxide, myristyl dimethyl amine oxide, cetyl dimethyl amine oxide, stearyl dimethyl amine oxide, lauryl morpholine oxide, bi-(2-hydroxyethyl) stearyl amine oxide, and (b) Lauroyl and myristoyl diethanolamide and lauroyl diisopropanolamide.

B. Foam Generating Agent

The volatile component used to generate the foam is selected from the group consisting of saturated hydrocarbons, saturated fluorocarbons and mixtures of these that boil in the range of 20° and 40° C. at normal atmospheric pressure. Members of this group include n-pentane (B.P. 36° C. and isopentane (B.P. 28° C.). Isopentane is preferred either alone or as the dominant component of a mixture of foam-generating agents.

It has been found that with the compositions having the same boiling point, the one with the lowest-boiling-point foam-generating agent will generate a lather most readily. This is the reason isopentane is preferred over n-pentane. However, if the boiling point of the foam-generation agent is very low, excessive amounts of vapor-pressure depressant may be required to raise the boiling point of the composition above about 50C.

The composition should contain from about 2 to 8% by weight of the foam-generating agent.

C. Nonvolatile, Water-insoluble Organic Liquid

Any of a broad range of organic liquids that are nonvolatile and water-insoluble can be used in combination with the aqueous soap solution and the foam-generating agent. These organic liquids are miscible with the foam-generating agent and they facilitate the dissolution of the free fatty acids in the non-aqueous phase, and thus promote the effectiveness of the free fatty acids in raising the boiling point. When used in combination with the aqueous soap solutions and foam-generating agents of this invention, the observed boiling point is higher than the expected boiling point and the increase is dependent on the percent of fatty acids in the composition.

Table 2 shows that with various types of nonvolatile, water-insoluble organic liquids the boiling points of the compositions are substantially greater than the expected values. The latter boiling points were obtained from curves in FIG. 1.

Figure 1:
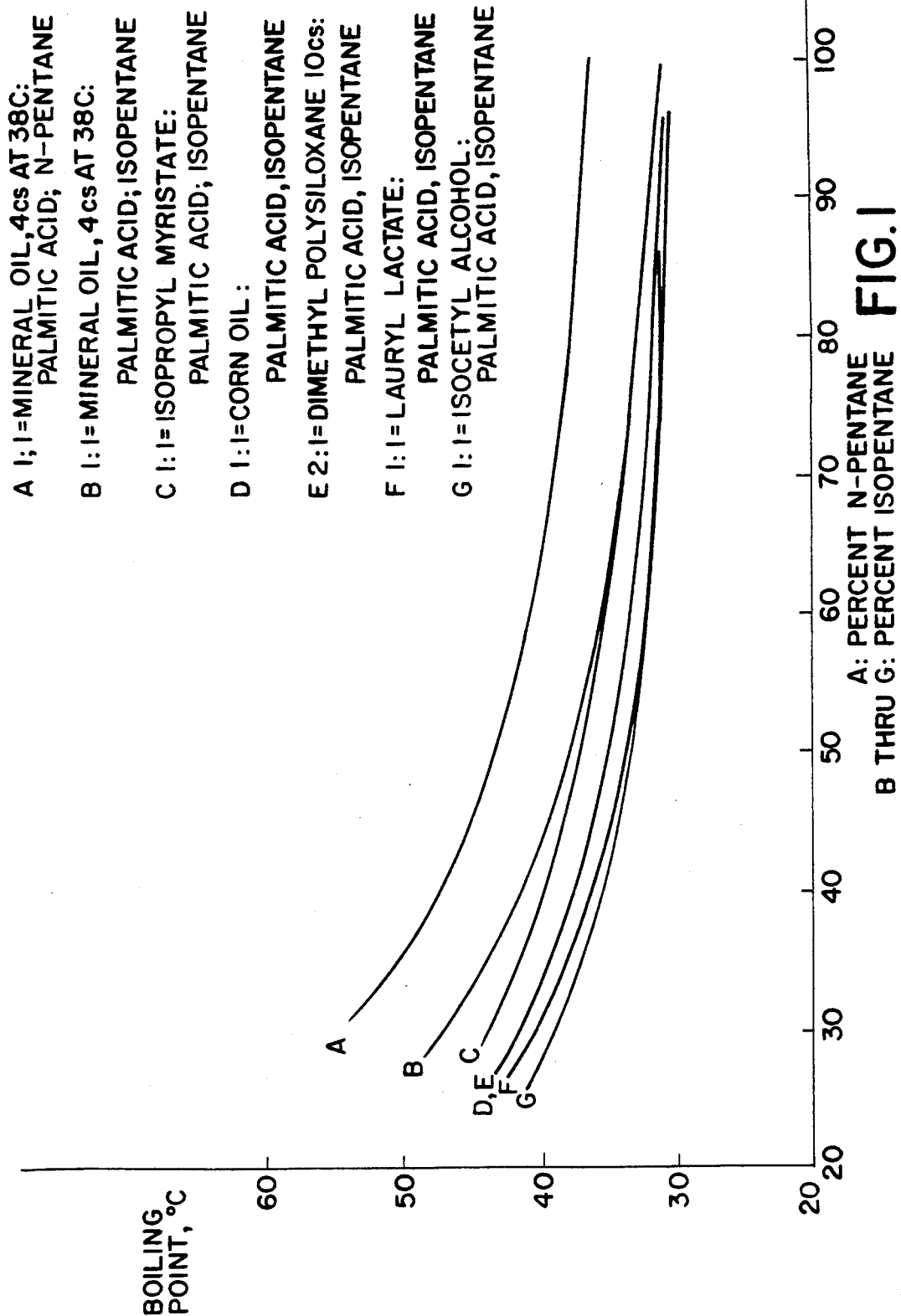
FIG. 1 was constructed from data obtained by determining the boiling points of solutions of a foam-generating agent in nonvolatile, water-insoluble organic liquid containing dissolved palmitic acid.

Low viscosity mineral oil was the most effective organic liquid found for raising the boiling point of the foam-generating agent, as shown in FIG. 1. In addition, it was found to give the most stable lathers.

The nonvolatile, water-insoluble organic liquids should be used at a concentration in the range of about 1 to about 10% by weight, based on the total weight of the composition. At least about 1% is required for dissolution of the free fatty acids. This can be seen from Table 3. With isopentane, both 1.9 and 2.9% of mineral oil, 4 cs at 38 degrees C., give the same increase in boiling point over the expected value, while 0.9% of that mineral oil gives a substantially lower increase. With n-pentane, a similar large increase over the expected boiling point is obtained with 1.1% of the same mineral oil.

If the amount of nonvolatile, water-insoluble organic liquid is too high, both product stability and lather stability will be adversely affected. The preferred organic liquid is a low viscosity mineral oil. The viscosity of the mineral oil should preferably be in the range of 4 to 40 cs. at 38 degrees C.

D. Adjuvant Ingredients

In addition to these essential ingredients, various adjuvant ingredients customarily used in shaving preparations may be incorporated. These include humectants, such as glycerine, propylene glycol and sorbitol, emollients such as lecithin and lanolin, corrosion inhibitors such as sodium and potassium silicates, preservatives such as the methyl and propyl esters of p-hydroxybenzoic acid, dyes and fragrances.

E. Overall Requirements

This invention deals with shaving compositions that boil above about 50° C. at atmospheric pressure, and when rubbed on the face rapidly develop a shaving lather. The composition consists of:

(1) from about 85 to 96% by weight of an aqueous soap solution containing from about 14 to about 20% by weight based on the total weight of the composition of fatty acids where from about 50 to 85% of the fatty acids have been neutralized to form water-soluble soaps. The neutralizing agent is preferably triethanolamine. The fatty acids are predominantly palmitic and stearic acids. If so desired a minor portion of the fatty acids may be replaced by a surfactant. If surfactants are present they are preferably selected from the group consisting of tertiary amine oxides with one hydrocarbon chain of 12 to 22 carbon atoms and lauroyl and myristoyl dialkanolamides. The concentration of soap is greater than that of the surfactant in the aqueous solution. Other superfatting agents may replace part of the unneutralized or free fatty acids.

(2) from about 2 to 8% by weight of a volatile organic liquid selected from the group consisting of saturated hydrocarbons, saturated fluorocarbons and mixtures of these that boil normally in the range of 20 to 40 degrees C. Preferably, isopentane is the sole or predominant foam-generating agent. It is preferably used at a concentration of 2 to 5% by weight.

(3) from about 1 to 10% by weight of a non-volatile, water-insoluble liquid. Preferably, this liquid is a low-viscosity mineral oil having a viscosity in the range of about 4 to 40 cs at 38 degrees C. Other non-volatile, water-insoluble liquids may be included in the composition.

The proportions of ingredients are selected in accordance with the teachings of this invention to provide a composition that rapidly generates a stable lather and that does not boil below 50 degrees C.

The compositions may be packaged in any type of package that is suitable for their consistency. Since the compositions contain a volatile component, the walls of the container as well as seals and closures must act as effective barriers. Most commonly, the compositions are gels and they may be packaged in collapsible tubes as well as suitable jars and pumps and squeeze pumps containing an inner barrier bag. Collapsible tubes may include aluminum, coated aluminum, tin-plate, wax-lined lead, and laminated tubes with an appropriate barrier layer.

The examples that follow illustrate the invention. All compositions were prepared in essentially the same way. Deionized water was boiled to remove dissolved air. The fatty acids, surfactants and ancillary ingredients such as humectants, preservatives, corrosion inhibitors and dyes were then added. Only the alkaline neutralizing agent, fragrance, water-insoluble oils and foam-generating agent were withheld. With the mixture maintained at 70 to 75 degrees C. the alkaline neutralizing agent was added while stirring. The stirrer was fitted with a baffle to avoid formation of a vortex and the introduction of air during stirring. After all of the alkali had been added, the composition was cooled to 0 to 5 degrees C. with slow stirring. A vacuum was applied during cooling to remove any dissolved or dispersed air. Water lost by evaporation was replaced by preboiled and chilled deionized water. Fragrance, water-insoluble oils and the foam-generating agent were added, with further cooling to maintain the temperature at 0–5 degrees C. and slow stirring until the composition appeared uniform. It was then packaged.

While a batch process has been described here for the preparation of the compositions of this invention, a continuous process may also be used.

EXAMPLE 1

|  | Parts By Weight |
|---|---|
| Palmitic acid | 9.56 |
| Coconut fatty acids | 5.55 |
| Triethanolamine | 6.18 |
| Lauroyl diethanolamide | 1.71 |
| Propylene glycol | 4.18 |
| Methyl p-hydroxybenzoate | 0.2 |
| Propyl p-hydroxybenzoate | 0.1 |
| Water | 63.05 |
| Fragrance | 0.5 |
| Mineral Oil, 4 cs at 38 degrees C. | 4.46 |
| Isopentane | 4.50 |
|  | 100.00 |

This composition contains 16.8% fatty acids plus surfactant. Of the 15.1% fatty acids, 34 mole % is present as free fatty acids. Thus the composition contains 16.1% soap and 5.1% free fatty acids. The boiling point was determined to be 59 degrees C. as compared with a value of 42 degrees C. from curve B of FIG. 1. When rubbed on the face, it began to lather within a few seconds from the start of the application and formed a stable shaving cream lather.

EXAMPLE 2

|  | Parts By Weight |
|---|---|
| Palmitic acid | 10.99 |
| Coconut fatty acids | 4.18 |
| Diethanolamine | 3.43 |
| Lauroyl diethanolamide | 1.76 |
| Propylene glycol | 4.27 |
| Methyl p-hydroxybenzoate | 0.20 |
| Propyl p-hydroxybenzoate | 0.10 |
| Water | 63.70 |
| Fragrance | 0.50 |
| Mineral Oil, 4 cs at 38 degrees C. | 4.25 |
| Corn oil | 2.12 |
| Isopentane | 4.50 |
|  | 100.00 |

This composition contains 16.9% fatty acids plus surfactant. Total fatty acids are 15.2%, of which 50 mole % are present as free fatty acids. Thus the composition contains 11% soap and 7.6% free fatty acids. The boiling point was determined to be 59 degrees C. as compared with the value of 44 degrees C. extrapolated from curves B and D of FIG. 1. When rubbed on the face, it began to lather within a few seconds from the start of the application and it formed a stable shaving cream lather.

EXAMPLE 3

|  | Parts By Weight |
|---|---|
| Palmitic acid | 9.92 |
| Coconut fatty acids | 5.88 |
| Triethanolamine | 6.67 |
| Propylene glycol | 4.21 |
| Methyl p-hydroxybenzoate | 0.20 |
| Propyl p-hydroxybenzoate | 0.10 |
| Water | 63.56 |
| Fragrance | 0.50 |

-continued

|  | Parts By Weight |
|---|---|
| Mineral Oil, 4 cs at 38 degrees C. | 4.46 |
| Isopentane | 4.50 |
|  | 100.00 |

This composition contains 15.8% fatty acids of which 31% are present as free fatty acids. This corresponds to 17.6% soap and 4.9% free fatty acids based on the total composition. The boiling point was determined to be 57 degrees C. as compared with the value of 45 degrees C. from curve B of FIG. 1. When rubbed on the face, it began to lather within a few seconds from the start of the application and it formed a stable shaving cream lather.

EXAMPLE 4

|  | Parts By Weight |
|---|---|
| Palmitic acid | 10.57 |
| Coconut fatty acids | 7.50 |
| Triethanolamine | 7.69 |
| Propylene glycol | 4.11 |
| Methyl p-hydroxybenzoate | 0.20 |
| Propyl p-hydroxybenzoate | 0.10 |
| Water | 61.83 |
| Fragrance | 0.50 |
| Mineral Oil, 4 cs at 38 degrees C. | 4.50 |
| Isopentane | 3.00 |
|  | 100.00 |

This composition contains 18% fatty acids of which 31% are present as free fatty acids. This corresponds to 20% soap and 5.6% free fatty acids based on the total composition. The boiling point was determined to be 64 degrees C. as compared with a value of 51 degrees C. obtained by extending curve B of FIG. 1. Boiling points much above 60 degrees C. could not be determined accurately, possibly because the soap structure responsible disrupted at these high temperatures.

When rubbed on the face, the shaving composition began to lather within a few seconds from the start of the application and it formed a stable shaving cream lather.

EXAMPLE 5

|  | Parts By Weight |
|---|---|
| Palmitic acid | 10.02 |
| Coconut fatty acids | 7.11 |
| Triethanolamine | 7.29 |
| Propylene glycol | 3.90 |
| Methyl p-hydroxybenzoate | 0.20 |
| Propyl p-hydroxybenzoate | 0.10 |
| Water | 58.78 |
| Fragrance | 0.50 |
| Mineral Oil, 4 cs at 38 degrees C. | 7.60 |
| Isopentane | 3.00 |
| n-Pentane | 1.50 |
|  | 100.00 |

This composition contains 17.1% fatty acids of which 31% are present as free fatty acids. This corresponds to 19% soap and 5.3% free fatty acids. The boiling point was determined to be above 65° C. As with Example 4, boiling points much above 60° C. could not be determined accurately. The expected comparison value of 53° C. was obtained by extending curves A and B of FIG. 1 and extrapolating between them.

When rubbed on the face, the shaving composition began to lather within a few seconds from the start of the application and it formed a fairly stable shaving cream lather.

What is claimed is:

1. A shaving composition boiling above about 50° C. that rapidly generates a stable lather when rubbed on the skin consisting of:
    a) from about 85 to 96% by weight of an aqueous soap solution of a soap selected from the group consisting of triethanolamine soaps and diethanolamine soaps, said soap solution containing about 14 to about 20% by weight based on the total weight of the composition of fatty acids, where from about 50 to 85% of the fatty acids have been neutralized to form said soaps, and at least about 50% of the fatty acids are palmitic and/or stearic acid and the remainder are primarily lauric and/or myristic acid,
    b) from about 2 to 8% by weight of a volatile organic liquid selected from the group consisting of isopentane, n-pentane and mixtures of the two,
    c) from about 1 to 10% by weight of a nonvolatile, water insoluble organic liquid, and where (a) plus (b) plus (c) equal 100% by weight of the composition, and the boiling point of the volatile organic liquid is increased to above about 50° C., the increase being due in substantial part to the aqueous soap solution, as well as to the presence of free fatty acids and nonvolatile organic liquid in the same liquid phase as the volatile organic liquid.

2. A shaving preparation according to claim 1 wherein the soap is a triethanolamine soap.

3. A shaving preparation according to claim 1 wherein the nonvolatile, water-insoluble organic liquid is a mineral oil with a viscosity of about 4 to 40 cs at 38° C.

4. A shaving composition boiling above about 50° C. that rapidly generates a stable lather when rubbed on the skin consisting of:
    a) from about 85 to 96% by weight of an aqueous soap solution of a soap selected from the group consisting of triethanolamine soaps and diethanolamine soaps, said soap solution containing about 14 to about 20% by weight based on the total weight of the composition of fatty acids, where from about 50 to 85% of the fatty acids having either been neutralized to form said soaps, or up to 35% of the fatty acids have been replaced by a surfactant that is predominately from the group consisting of long hydrogen chain tertiary amine oxides and lauroyl and myristoyl alkanolamides and at least about 50% of the fatty acids are palmitic and/or stearic acid and the remainder are primarily lauric and/or myristic acid,
    b) from about 2 to 8% by weight of a volatile organic liquid selected from the group consisting of isopentane, n-pentane and mixtures of the two,
    c) from about 1 to 10% by weight of a nonvolatile, water insoluble organic liquid, and
where (a) plus (b) plus (c) equal 100% by weight of the composition, and the boiling point of the volatile organic liquid is increased to above about 50° C., the increase being due in substantial part to the aqueous soap solution, as well as to the presence of free fatty acids and nonvolatile organic liquid in the same liquid phase as the volatile organic liquid.

5. A shaving composition boiling above about 50° C. that rapidly generates a stable lather when rubbed on the skin consisting of:
    a) from about 85 to 96% by weight of an aqueous soap solution of a soap selected from the group consisting of triethanolamine soaps and diethanolamine soaps, said soap solution containing about 14 to about 20% by weight based on the total weight of the composition of fatty acids, where from about 50 to 85% of the fatty acids have been neutralized to form said soaps, and at least about 50% of the fatty acids are palmitic and/or stearic acid and the remainder are primarily lauric and/or myristic acid,
    b) from about 2 to 8% by weight of a volatile organic liquid selected from the group consisting of a mixture of isopentane and n-pentane wherein the amount of isopentane is greater than the amount of n-pentane.
    c) from about 1 to 10% by weight of a nonvolatile, water insoluble organic liquid, and
where (a) plus (b) plus (c) equal 100% by weight of the composition, and the boiling point of the volatile organic liquid is increased to above about 50° C., the increase being due in substantial part to the aqueous soap solution, as well as to the presence of free fatty acids and nonvolatile organic liquid in the same liquid phase as the volatile organic liquid.

* * * * *